US012319952B2

(12) United States Patent
Li et al.

(10) Patent No.: US 12,319,952 B2
(45) Date of Patent: Jun. 3, 2025

(54) METHOD FOR ENZYMATIC RESOLUTION OF CHIRAL SUBSTANCES

(71) Applicant: South China University of Technology, Guangzhou (CN)

(72) Inventors: Zhigang Li, Guangzhou (CN); Jinfen Su, Guangzhou (CN); Bo Yang, Guangzhou (CN); Yonghua Wang, Guangzhou (CN); Zhengcheng Li, Guangzhou (CN); Huayong Chen, Guangzhou (CN)

(73) Assignee: South China University of Technology, Guangzhou (CN)

( * ) Notice: Subject to any disclaimer, the term of this patent is extended or adjusted under 35 U.S.C. 154(b) by 1026 days.

(21) Appl. No.: 17/311,835

(22) PCT Filed: Oct. 25, 2019

(86) PCT No.: PCT/CN2019/113139
§ 371 (c)(1),
(2) Date: Jun. 8, 2021

(87) PCT Pub. No.: WO2020/119280
PCT Pub. Date: Jun. 18, 2020

(65) Prior Publication Data
US 2022/0017935 A1 Jan. 20, 2022

(30) Foreign Application Priority Data
Dec. 10, 2018 (CN) .......................... 201811500754.8

(51) Int. Cl.
*C12P 41/00* (2006.01)
*C12N 9/20* (2006.01)
*C12P 7/04* (2006.01)
*C12P 7/22* (2006.01)
*C12P 7/40* (2006.01)
*C12P 7/42* (2006.01)
*C12P 7/62* (2022.01)
*C12P 13/02* (2006.01)

(52) U.S. Cl.
CPC .............. *C12P 41/001* (2013.01); *C12N 9/20* (2013.01); *C12P 7/04* (2013.01); *C12P 7/22* (2013.01); *C12P 7/40* (2013.01); *C12P 7/42* (2013.01); *C12P 7/62* (2013.01); *C12P 41/004* (2013.01); *C12P 41/005* (2013.01); *C12P 13/02* (2013.01); *C12Y 301/01003* (2013.01); *C12Y 301/01074* (2013.01)

(58) Field of Classification Search
CPC .. C12P 41/001; C12P 7/04; C12P 7/22; C12P 7/40; C12P 7/42; C12P 7/62; C12P 41/004; C12P 41/005; C12P 13/02; C12N 9/20; C12Y 301/01003; C12Y 301/01074
See application file for complete search history.

(56) References Cited

U.S. PATENT DOCUMENTS

| 5,342,780 A | 8/1994 | Morrow et al. |
| 5,928,933 A | 7/1999 | Dicosimo et al. |

FOREIGN PATENT DOCUMENTS

| CN | 1329671 A | 1/2002 |
| CN | 101220382 A | 7/2008 |
| CN | 102559520 A | 7/2012 |
| CN | 103184245 A | 7/2013 |
| CN | 105506052 A | 4/2016 |
| CN | 106520898 A | 3/2017 |
| CN | 109628508 A | 4/2019 |

(Continued)

OTHER PUBLICATIONS

Takac, S. et al. Impressive effect of immobilization conditions on the catalytic activity and enantioselectivity of Candida rugosa lipase toward S-Naproxen production, 2007, Process Biochemistry, 42(6): 1021-1027 (Year: 2007).*
Chemical Communications; Substrate-constituted three-liquid-phase system: a green, highly efficient and recoverable platform for interfacial enzymatic reaction; www.rsc.org/chemcomm.
Hydrolysis of olive oil by lipase in three liquid phase system; Chen, Hua.
Progress in research on three phase extraction (Liquid-Liquid-Liquid) and its application in separation of biochemical products; Tan Xiandong.

*Primary Examiner* — Louise W Humphrey
*Assistant Examiner* — Charles Zoltan Constantine
(74) *Attorney, Agent, or Firm* — The Dobrusin Law Firm, PC

(57) ABSTRACT

The invention belongs to the field of bioengineering and food technology, and discloses a method for enzymatic resolution of chiral substances, including the following steps: (1) preparing an enzyme solution with a lipase concentration of 1-3000 U/mL, and adding a soluble salt, a hydrophilic solvent and a hydrophobic solvent to the enzyme solution to form a three-liquid phase system; the hydrophobic solvent contains esters or amide compounds composed of racemic chiral compounds; (2) subjecting the three-liquid phase system to enzyme-catalyzed reaction under stirring condition; after the reaction is completed, standing or centrifuging the three-liquid phase system to divide it into three layers, which are a upper liquid layer, a middle liquid layer and a lower liquid layer from top to bottom. The optically pure chiral product after hydrolysis is mainly rich in the middle liquid layer or the lower liquid layer, while the upper liquid layer product is another ester or amide product containing an optically pure chiral product. The method has the advantages of low energy consumption, high raw material utilization rate, and mild reaction conditions, and solves the problems of low chiral resolution efficiency, poor chiral selectivity, low recovery rate, and difficulty in industrialization in the existing enzymatic method.

20 Claims, No Drawings

(56) References Cited

FOREIGN PATENT DOCUMENTS

EP 0414569 A2 2/1991
WO 2009/153325 A1 12/2009

* cited by examiner

METHOD FOR ENZYMATIC RESOLUTION OF CHIRAL SUBSTANCES

TECHNICAL FIELD

The invention belongs to the field of bioengineering and food technology, and relates to the separation and application of enzymes, and particularly relates to a method for enzymatic resolution of chiral substances.

BACKGROUND

In recent decades, chiral substances have been rapidly developed. More than two-thirds of the drugs being developed in the world are chiral drugs, the current market size of which has exceeded US$250 billion. It has become an inevitable trend to replace traditional mixed racemic drugs with single chiral drugs with higher efficacy and fewer side effects. Although China has significant demand insufficiency and related basic resources for chiral materials, due to the backward technology and poor product quality, most of the related products are difficult to compete with western countries, and industrial upgrading is urgently needed.

At present, the preparation of single configuration isomers is mainly through induced crystallization or chemical resolution methods to resolve racemates. Traditional processes usually use chiral resolution agents for resolution, which is low in efficiency and requires repeated refining to meet the standard, leading to the extremely complicated process and extremely high cost of the whole process (J. Mol. Catal. B: Enzym., 2010, 62(2): 162-168, Org. Biomol. Chem., 2014, 12, 6634-6642, J. Mol. Catal. B: Enzym., 2010, 65(1/4):49-51). Enzymatic resolution has the advantages of mild conditions and high product purity, and is highly expected. However, on one hand, the physical and chemical properties of the chiral product and its enantiomeric by-product are too close, making it difficult to separate the product from the by-product by conventional separation methods to improve reaction selectivity. Although the extraction resolution by adding a chiral selective agent has certain potential, lipase catalysis belongs to interfacial catalysis, such that even in a two-phase system, the product may have a strong inhibitory effect on the reaction. Therefore, it is difficult to use the existing system to relieve product inhibition and to improve catalytic efficiency. On the other hand, chiral resolution requires extremely high optical purity of the product. Under normal circumstances, the purity of mono-optical products is usually greater than 99%. As the reaction progresses, the target substrate content gradually decreases and the product gradually accumulates, leading to problems such as side reactions, low product purity and poor conversion rate in most reactions. Therefore, enzymes with high selectivity (usually E≥100) only in a few reaction have the potential for industrialization, which greatly increases the difficulty of research and development (Tetrahedron 2007, 63: 1721-1754). In addition, traditional enzyme catalytic systems still have problems in difficulty in control, and incompatibility in product separation and enzyme reuse, which severely restricts its development. Therefore, it is urgent to develop an efficient and controllable catalysis and separation system to suit its development (Journal of Molecular Catalysis B: Enzymatic, 2012, 4:78-82, Tetrahedron 2007, 63: 1721-1754).

SUMMARY OF THE INVENTION

The purpose of the present invention is to solve the problems of high cost, difficulty in continuous production, low reaction efficiency and long reaction time caused by product inhibition in the current process of enzymatic resolution and production of chiral substances, and to provide an efficient and rapid enzymatic resolution method for chiral substances.

The purpose of the present invention is achieved through the following technical solutions:

A method for enzymatic resolution of chiral substances comprises the following steps:

(1) preparing an enzyme solution with a lipase concentration of 1-3000 U/mL, adding a soluble salt, a hydrophilic solvent and a hydrophobic solvent to the enzyme solution to form a three-liquid phase system; the mass ratios of the soluble salt, the hydrophilic solvent and the hydrophobic solvent to the enzyme solution are 0.1-0.9, 0.1-5 and 0.1-10, respectively; the hydrophobic solvent contains an ester or amide compound composed of a racemic chiral compound;

(2) subjecting the three-liquid phase system to enzyme-catalyzed reaction under stirring condition; after the reaction, standing or centrifuging the three-liquid phase system until it is divided into three layers, which are a upper liquid layer, a middle liquid layer and a lower liquid layer from top to bottom; hydrolyzed optically pure chiral product is mainly concentrated in the middle liquid layer or the lower liquid layer, and the upper liquid layer product is another ester or amide product containing an optically pure chiral product.

Preferably, the hydrophilic solvent in step (1) is one or more of polyethylene glycol, polypropylene glycol, ethanol, n-propanol, isopropanol, n-butanol, isobutanol, ethylene glycol and acetone; or the hydrophilic solvent is one or more of [BMIM]Br, [BMIM]BF$_4$, [EMIM]ETSO$_4$ and [OMIM]Cl.

Preferably, the soluble salt in step (1) is one or more of sodium citrate, sodium chloride, ammonium sulfate, sodium carbonate, dipotassium hydrogen phosphate, potassium phosphate, potassium dihydrogen phosphate and dipotassium hydrogen phosphate.

Preferably, the hydrophobic solvent in step (1) is one or more of n-hexane, diethyl ether, isopropyl ether, ethyl acetate, cyclohexanol, petroleum ether, isooctane, benzene and toluene.

The reaction is generally carried out at a temperature lower than the volatile temperature of the solvent. In order to achieve the best possible removal and modification effects of chiral products, the pH value of the system can be adjusted. Preferably, the reaction conditions of step (2) are: a temperature of 30-45° C., and a reaction time of 20 min-4 h.

Preferably, the pH value of the three-liquid phase system in step (1) is 5-9.

Preferably, the lipase concentration in step (1) is 5-2000 U/mL.

Preferably, the mass ratios of the soluble salt, hydrophilic solvent and hydrophobic solvent to the enzyme solution are 0.2-0.8, 0.2-0.8 and 0.2-4, respectively.

Preferably, the ester or amide compound composed of the racemic chiral compound is one or more of racemic methyl mandelate, racemic Naproxen methyl ester, racemic (4-methoxy-phenyl)-1-ethanol acetate, racemic 1-(4-methoxyphenyl) ethanol acetate, and racemic 6-methyl-5-heptenyl-2-ol acetate.

Preferably, the ester or amide compound composed of the racemic chiral compound accounts for 0.1%-10% of the mass of the hydrophobic solvent, preferably 1%-5%.

In the above lipase-catalyzed reaction, the lipase may be natural or produced through artificial fermentation. It can be fermentation broth, crude enzyme after simple purification, or pure enzyme after purification.

The beneficial effects of the present invention are as follows:

The invention overcomes the problems of high cost, difficulty in continuous production, low reaction efficiency and long reaction time caused by product inhibition in the current process of enzymatic resolution and synchronous recovery of chiral substances, and provides a method for separating lipase from raw enzyme solution and using lipase for resolution of chiral substances. The process is simplified, short in separation time, low in cost, and economically feasible, specifically: the use of a three-liquid phase system can distribute an optically pure chiral product ester or amide substrate in the hydrophobic phase, while the lipase is distributed in the solvent-rich phase or salt-rich phase, wherein the hydrolyzed optically pure chiral substances is mainly concentrated in another phase, and the product can be recycled by simple centrifugation or standing. This process not only facilitates the purification and recovery of the enzyme, but also improves the catalytic efficiency and greatly reduces the loss and purification cost of the enzyme. The method has the advantages of low energy consumption, high raw material utilization rate, mild reaction conditions, etc., and solves the technical problem that the existing enzymatic separation and production of chiral substances are difficult to industrialize.

DETAILED DESCRIPTION

The present invention will be further specifically described in detail below in conjunction with specific examples, but the implementation of the present invention is not limited to this, and the process parameters that are not specifically noted can be carried out with reference to conventional techniques.

In the examples, CALB (*Candida antarctica* lipase B) and Novozyme-51032 (cutinase) lipase used were purchased from Novozyme, and lipase AY30 (*Candida rugosa* lipases) was purchased from Amano, Japan.

Example 1

Mix an appropriate amount of CALB lipase and water with 1000 times the volume of the lipase in an Erlenmeyer flask; mix 1 g of the crude enzyme solution (enzyme concentration 5 U/mL) and 0.6 g of dipotassium hydrogen phosphate, add 0.4 g of polyethylene glycol 400 and 0.4 g of isopropyl ether solution containing 5% racemic methyl mandelate, and mix them in a stoppered Erlenmeyer flask, wherein the pH of the mixed solution was 8.9; place it on a constant temperature shaker with a rotation speed of 200 rpm, react at 30° C. for 2 h. Take another 1 g of the crude enzyme solution (5 U/mL), add 0.4 g of isopropyl ether solution containing 5% racemic methyl mandelate, dilute with water to the same volume, and react under the same conditions as a control. After the reaction was over, centrifuge at 5000 rpm for 5 minutes and divide into three layers, which were upper liquid layer, middle liquid layer and lower liquid layer. The optically pure chiral product after hydrolysis was mainly concentrated in the middle liquid layer or the lower liquid layer, and the collected upper liquid layer product was another optically pure chiral ester or amide product. Lipase was mainly distributed in the middle liquid layer, and the distribution coefficient of the middle and lower liquid layer can reach 4.75. In addition, the middle and lower liquid layer was used to measure the enzyme activity, and the upper liquid layer was used to determine optical rotation degree of methyl mandelate. It was found that the optical rotation degree of S-mandelic acid methyl ester in the hydrophobic phase reached 99.5%, while the control group was only divided into upper and lower phases, wherein the product was distributed in both phases, and the total optical rotation degree of S-mandelic acid methyl ester was only 43%.

Example 2

Mix an appropriate amount of AY30 lipase and water with 100 times the volume of the lipase in an Erlenmeyer flask; mix 0.975 g of the crude enzyme solution (enzyme concentration 100 U/mL) and 0.225 g of sodium sulfate, add 0.3 g of polyethylene glycol 400 and 0.3 g of isooctane solution containing 0.5% racemic naproxen methyl ester, and mix them in a stoppered Erlenmeyer flask, wherein the pH of the mixed solution was 7.0; place it on a constant temperature shaker with a rotation speed of 200 rpm, react at 37° C. for 4 h. Take another 0.975 g of the crude enzyme solution (200 U/mL), add 0.3 g of isooctane solution containing 0.5% racemic naproxen methyl ester, dilute with water to the same volume, and react under the same conditions as a control. After the reaction was over, centrifuge at 3000 rpm for 1 minutes and divide into three layers, which were upper liquid layer, middle liquid layer and lower liquid layer. The optically pure chiral product after hydrolysis was mainly concentrated in the middle liquid layer, and the collected upper liquid layer product was another optically pure chiral ester or amide product. Lipase was mainly distributed in the middle liquid layer, and the distribution coefficient of the middle and lower liquid layer can reach 48.9. It was found that the optical rotation and enantiomeric selectivity E value of the R-naproxen product in the system reached 92.9% and 46, respectively, while the control group was only divided into upper and lower phases, wherein the product was distributed in both the two phases, and the optical rotation and the enantiomeric selectivity E value were only 86.5% and 18.

Example 3

Mix an appropriate amount of AY30 lipase and water with 100 times the volume of the lipase in an Erlenmeyer flask; mix 0.975 g of the crude enzyme solution (enzyme concentration 100 U/mL) and 0.24 g of sodium sulfate, add 0.3 g of polyethylene glycol 400 and 0.3 g of isooctane solution containing 0.5% racemic (4-methoxy-phenyl)-1-ethanol acetate, and mix them in a stoppered Erlenmeyer flask, wherein the pH of the mixed solution was 7.0; place it on a constant temperature shaker with a rotation speed of 200 rpm, react at 45° C. for 20 min. Take another 0.975 g of the crude enzyme solution (100 U/mL), add 0.3 g of isooctane solution containing 0.5% racemic (4-methoxy-phenyl)-1-ethanol acetate, dilute with water to the same volume, and react under the same conditions as a control. After the reaction was over, centrifuge at 9000 rpm for 3 minutes and divide into three layers, which were upper liquid layer, middle liquid layer and lower liquid layer. The optically pure chiral product after hydrolysis was mainly concentrated in the middle liquid layer, and the collected upper liquid layer product was another optically pure chiral ester or amide product. Lipase was mainly distributed in the middle liquid layer, and the distribution coefficient of the middle and lower liquid layer can reach 149.1. It was found that the optical rotation and enantiomeric selectivity E value of the (4-methoxy-phenyl)-1-ethanol acetate in the system reached 98.13% and 232.8, respectively, while the control group was only divided into upper and lower phases, wherein the product was distributed in both the two phases, and the optical rotation and the enantiomeric selectivity E value were only 94.13% and 69.39.

Example 4

Mix an appropriate amount of AY30 lipase and water with 100 times the volume of the lipase in an Erlenmeyer flask; mix 0.975 g of the crude enzyme solution (enzyme concentration 100 U/mL) and 0.225 g of sodium sulfate, add 0.3 g of [BMIm]BF$_4$ and 0.3 g of isooctane solution containing 0.5% racemic naproxen methyl ester, and mix them in a stoppered Erlenmeyer flask; place it on a constant temperature shaker with a rotation speed of 200 rpm, react at 37° C. for 4 h. After the reaction was over, centrifuge at 3000 rpm for 1 minutes and divide into three layers, which were upper liquid layer, middle liquid layer and lower liquid layer. The optically pure chiral product after hydrolysis was mainly concentrated in the middle liquid layer, and the collected upper liquid layer product was another optically pure chiral ester product. Lipase was mainly distributed in the lower liquid layer, and the enzyme recovery rate of the lower liquid layer can reach 98.5%. The optical rotation and enantiomeric selectivity E value of the R-naproxen product in the system also reached 82.1% and 11, respectively.

Example 5

Mix an appropriate amount of Novozyme-51032 lipase and water with 100 times the volume of the lipase in an Erlenmeyer flask; mix 0.975 g of the crude enzyme solution (enzyme concentration 5 U/mL) and 0.24 g of sodium sulfate, add 0.285 g of polyethylene glycol 400 and 0.3 g of n-hexane solution containing 0.5% racemic 1-(4-methoxy-phenyl)ethanol acetate, and mix them in a stoppered Erlenmeyer flask, wherein the pH of the mixed solution was 7.0; place it on a constant temperature shaker with a rotation speed of 9000 rpm, react at 45° C. for 20 min. Take another 0.975 g of the crude enzyme solution (5 U/mL), add 0.3 g of n-hexane solution containing 0.5% racemic 1-(4-methoxyphenyl)ethanol acetate, dilute with water to the same volume, and react under the same conditions as a control. After the reaction was over, centrifuge at 9000 rpm for 3 minutes and divide into three layers, which were upper liquid layer, middle liquid layer and lower liquid layer. The optically pure chiral product after hydrolysis was mainly concentrated in the middle liquid layer, and the collected upper liquid layer product was another optically pure chiral ester or amide product. In addition, the middle and lower liquid layer were used to measure the enzyme activity, and the upper liquid layer was used to determine optical rotation degree of 1-(4-methoxyphenyl)ethanol acetate. It was found that the optical rotation and enantiomeric selectivity E value of the 1-(4-methoxyphenyl)ethanol acetate in the hydrophobic phase reached 96.07% and 80.96, respectively, while the control group was only divided into upper and lower phases, wherein the product was distributed in both the two phases, and the optical rotation and the enantiomeric selectivity E value were only 85.72% and 17.01.

Example 6

Mix an appropriate amount of CALB lipase and water with 100 times the volume of the lipase in an Erlenmeyer flask; mix 0.975 g of the crude enzyme solution (enzyme concentration 5 U/mL) and 0.24 g of sodium sulfate, add 0.285 g of polyethylene glycol 400 and 0.3 g of n-hexane solution containing 0.5% 6-methyl 5-heptenyl 2-ol acetate, and mix them in a stoppered Erlenmeyer flask; place it on a constant temperature shaker with a rotation speed of 9000 rpm, react at 45° C. for 20 min. Take another 0.975 g of the crude enzyme solution (5 U/mL), add 0.3 g of n-hexane solution containing 0.5% 6-methyl 5-heptenyl 2-ol acetate, dilute with water to the same volume, and react under the same conditions as a control. After the reaction was over, centrifuge at 9000 rpm for 3 minutes and divide into three layers, which were upper liquid layer, middle liquid layer and lower liquid layer. The optically pure chiral product after hydrolysis was mainly concentrated in the middle liquid layer, and the collected upper liquid layer product was another optically pure chiral ester or amide product. In addition, the middle and lower liquid layer were used to measure the enzyme activity, and the upper liquid layer was used to determine optical rotation degree of 6-methyl 5-heptenyl 2-ol acetate. It was found that the optical rotation and enantiomeric selectivity E value of 6-methyl 5-heptenyl 2-ol acetate in the hydrophobic phase reached 96.49% and 72.85, respectively, while the control group was only divided into upper and lower phases, wherein the product was distributed in both the two phases, and the optical rotation and the enantiomeric selectivity E value were only 88.09% and 18.47.

Example 7

Mix an appropriate amount of CALB lipase and water with 100 times the volume of the lipase in an Erlenmeyer flask; mix 0.975 g of the crude enzyme solution (enzyme concentration 5 U/mL) and 0.24 g of sodium sulfate, add 0.285 g of polyethylene glycol 400 and 0.3 g of n-hexane solution containing 0.5% 1-(4-methylphenyl)ethanol acetate, and mix them in a stoppered Erlenmeyer flask; place it on a constant temperature shaker with a rotation speed of 9000 rpm, react at 45° C. for 20 min. Take another 0.975 g of the crude enzyme solution (5 U/mL), add 0.3 g of n-hexane solution containing 0.5% racemic 1-(4-methylphenyl)ethanol acetate, dilute with water to the same volume, and react under the same conditions as a control. After the reaction was over, centrifuge at 9000 rpm for 3 minutes and divide into three layers, which were upper liquid layer, middle liquid layer and lower liquid layer. The optically pure chiral product after hydrolysis was mainly concentrated in the middle liquid layer, and the collected upper liquid layer product was another optically pure chiral ester or amide product. It was found that the optical rotation and enantiomeric selectivity E value of 1-(4-methylphenyl)ethanol acetate in the system reached 95.87% and 156.87, respectively, while the control group was only divided into upper and lower phases, wherein the product was distributed in both the two phases, and the optical rotation and the enantiomeric selectivity E value were only 95.45% and 76.18.

Example 8

Mix an appropriate amount of AY30 lipase and water with 100 times the volume of the lipase in an Erlenmeyer flask; mix 0.9 g of the crude enzyme solution (enzyme concentration 100 U/mL) and 0.3 g of ammonium sulfate, add 0.3 g of polyethylene glycol 400 and 0.3 g of isooctane solution containing 0.5% racemic Naproxen methyl ester, and mix them in a stoppered Erlenmeyer flask; place it on a constant temperature shaker with a rotation speed of 200 rpm, react at 37° C. for 4 h. Take another 0.975 g of the crude enzyme solution (100 U/mL), add 0.3 g of isooctane solution containing 0.5% racemic Naproxen methyl ester, dilute with water to the same volume, and react under the same conditions as a control. After the reaction was over, centrifuge at 3000 rpm for 1 minutes and divide into three layers, which were upper liquid layer, middle liquid layer and lower liquid layer. The optically pure chiral product after hydrolysis was mainly concentrated in the middle liquid layer, and the collected upper liquid layer product was another optically pure chiral ester or amide product. Lipase was mainly distributed in the middle liquid layer, and the distribution coefficient of the middle and lower liquid layer can reach 21.4. It was found that the optical rotation and enantiomeric selectivity E value of the R-Naproxen methyl ester in the system reached 89.9% and 28, respectively, while the control group was only divided into upper and lower phases, wherein the product was distributed in both the two phases, and the optical rotation and the enantiomeric selectivity E value were only 86.5% and 18.

Example 9

Mix an appropriate amount of AY30 lipase and phosphate buffer (100 mM) with pH=8 having 100 times the volume of the lipase in an Erlenmeyer flask; mix 0.96 g of the crude enzyme solution (enzyme concentration 500 U/mL) and 0.18 g of sodium sulfate, add 0.36 g of polyethylene glycol 400 and 0.3 g of isooctane solution containing 0.5% racemic Naproxen methyl ester, and mix them in a stoppered Erlenmeyer flask; place it on a constant temperature shaker with a rotation speed of 200 rpm, react at 37° C. for 4 h. Take another appropriate amount of lipase AY30 and place it in an Erlenmeyer flask, add phosphate buffer (100 mM) having 20 times the volume of the lipase with pH values of 5 and 10, respectively, take 0.96 g of the crude enzyme solutions (500 U/mL), and prepare three-liquid phase systems by the same method as above, which had the same ratio but different pH values and were used as controls under the same conditions. After the reaction was over, centrifuge at 3000 rpm for 1 min and divide into three layers, which were upper liquid layer, middle liquid layer and lower liquid layer. The optically pure chiral product after hydrolysis was mainly concentrated in the middle liquid layer, and the collected upper liquid layer product was another optically pure chiral ester or amide product. Lipase was mainly distributed in the middle liquid layer. When the pH value was 8, the distribution coefficient of the middle and lower liquid layer can reach 88, while the control group was only 62 and 42, and the optical rotation degree of the R-naproxen product in the system can reach 98.5% having a conversion rate of 32%; when the pH value was 5, the optical rotation degree was only 92%; and when the pH value was 10, although similar optical rotation degree can be obtained, the conversion rate was only 12%.

The above-mentioned embodiments are preferred embodiments of the present invention, but the embodiments of the present invention are not limited by the above-mentioned embodiments, and any other changes, modifications, substitutions, combinations, and simplifications made without departing from the spirit and principle of the present invention all should be equivalent replacement methods, and they are all included in the protection scope of the present invention.

The invention claimed is:

1. A method for enzymatic resolution of chiral substances, characterized in that it comprises the following steps:
   (1) preparing an enzyme solution with a lipase concentration of 1-3000 U/mL, adding one or more soluble salts, one or more hydrophilic solvents and one or more hydrophobic solvents to the enzyme solution to form a three-liquid phase system;
   wherein the mass ratios of the soluble salts, the hydrophilic solvents and the hydrophobic solvents to the enzyme solution are 0.1-0.9, 0.1-5 and 0.1-10, respectively, and wherein the hydrophobic solvents contain one or more ester or amide compounds composed of one or more racemic chiral compounds;
   (2) subjecting the three-liquid phase system to enzyme-catalyzed reaction by stirring to hydrolyze one enantiomer of the racemic chiral compounds of each of the one or more esters or amides; and then
   (3) standing or centrifuging the three-liquid phase system until it is divided into three layers, which are an upper liquid layer, a middle liquid layer and a lower liquid layer, wherein the chiral product of the hydrolyzed enantiomer of the each ester or amide is concentrated in the middle liquid layer or the lower liquid layer, and the other enantiomer of each of the one or more esters or amides is concentrated in the upper liquid layer.

2. The method according to claim 1, characterized in that the hydrophilic solvents in step (1) are one or more of polyethylene glycol, polypropylene glycol, ethanol, n-propanol, isopropanol, n-butanol, isobutanol, ethylene glycol, acetone, 1-Butyl-3-methylimidazolium bromide ([BMIM]Br), 1-Butyl-3-methylimidazolium tetrafluoroborate ([BMIM]$BF_4$), 1-Ethyl-3-methylimidazolium ethyl sulfate ([EMIM]$ETSO_4$), and 1-methyl-3-octylmidazolium chloride ([OMIM]Cl).

3. The method according to claim 2, characterized in that the reaction conditions of step (2) are: a temperature of 30-45° C. and a reaction time of 20 min-4 h.

4. The method according to claim 3, characterized in that the pH value of the three-liquid phase system in step (1) is 5-9.

5. The method according to claim 2, characterized in that the ester or amide compounds composed of the racemic chiral compounds are one or more of racemic methyl mandelate, racemic Naproxen methyl ester, racemic (4-methoxy-phenyl)-1-ethanol acetate, racemic 1-(4-methoxyphenyl) ethanol acetate, and racemic 6-methyl-5-heptenyl-2-ol acetate.

6. The method according to claim 2, characterized in that the ester or amide compounds composed of the racemic chiral compounds accounts for 0.1%-10% of the mass of the hydrophobic solvents.

7. The method according to claim 1, characterized in that the soluble salts in step (1) are one or more of sodium citrate, sodium chloride, ammonium sulfate, sodium carbonate, potassium phosphate, potassium dihydrogen phosphate and dipotassium hydrogen phosphate.

8. The method according to claim 7, characterized in that the reaction conditions of step (2) are: a temperature of 30-45° C. and a reaction time of 20 min-4 h.

9. The method according to claim 7, characterized in that the ester or amide compounds composed of the racemic chiral compounds are one or more of racemic methyl mandelate, racemic Naproxen methyl ester, racemic (4-methoxy-phenyl)-1-ethanol acetate, racemic 1-(4-methoxyphenyl) ethanol acetate, and racemic 6-methyl-5-heptenyl-2-ol acetate.

10. The method according to claim 7, characterized in that the ester or amide compounds composed of the racemic chiral compounds accounts for 0.1%-10% of the mass of the hydrophobic solvents.

11. The method according to claim 1, characterized in that the hydrophobic solvents in step (1) are one or more of n-hexane, diethyl ether, isopropyl ether, ethyl acetate, cyclohexanol, petroleum ether, isooctane, benzene and toluene.

12. The method according to claim 11, characterized in that the reaction conditions of step (2) are: a temperature of 30-45° C. and a reaction time of 20 min-4 h.

13. The method according to claim 11, characterized in that the ester or amide compounds composed of the racemic chiral compounds are one or more of racemic methyl mandelate, racemic Naproxen methyl ester, racemic (4-methoxy-phenyl)-1-ethanol acetate, racemic 1-(4-methoxyphenyl) ethanol acetate, and racemic 6-methyl-5-heptenyl-2-ol acetate.

14. The method according to claim 11, characterized in that the ester or amide compounds composed of the racemic chiral compounds accounts for 0.1%-10% of the mass of the hydrophobic solvents.

15. The method according to claim 1, characterized in that the reaction conditions of step (2) are a temperature of 30-45° C., and a reaction time of 20 min-4 h.

16. The method according to claim 15, characterized in that the pH value of the three-liquid phase system in step (1) is 5-9.

17. The method according to claim 16, characterized in that the lipase concentration in step (1) is 5-2000 U/mL.

18. The method according to claim 17, characterized in that the mass ratios of the soluble salts, hydrophilic solvents and hydrophobic solvents to the enzyme solution are 0.2-0.8, 0.2-0.8 and 0.2-4, respectively.

19. The method according to claim 1, characterized in that the ester or amide compounds composed of the racemic chiral compounds are one or more of racemic methyl mandelate, racemic Naproxen methyl ester, racemic (4-methoxy-phenyl)-1-ethanol acetate, racemic 1-(4-methoxyphenyl) ethanol acetate, and racemic 6-methyl-5-heptenyl-2-ol acetate.

20. The method according to claim 1, characterized in that the ester or amide compounds composed of the racemic chiral compounds accounts for 0.1%-10% of the mass of the hydrophobic solvents.

* * * * *